United States Patent
Pflanz

(10) Patent No.: US 8,951,788 B2
(45) Date of Patent: Feb. 10, 2015

(54) FILTRATION UNIT AND METHOD FOR THE MICROBIOLOGICAL ANALYSIS OF LIQUID SAMPLES

(75) Inventor: Karl Pflanz, Gleichen (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 908 days.

(21) Appl. No.: 12/449,340

(22) PCT Filed: Feb. 16, 2008

(86) PCT No.: PCT/EP2008/001212
§ 371 (c)(1),
(2), (4) Date: Aug. 3, 2009

(87) PCT Pub. No.: WO2008/113443
PCT Pub. Date: Sep. 25, 2008

(65) Prior Publication Data
US 2010/0086959 A1    Apr. 8, 2010

(30) Foreign Application Priority Data
Mar. 21, 2007   (DE) .......................... 10 2007 014 082

(51) Int. Cl.
*C12M 1/12*     (2006.01)
*C12M 1/22*     (2006.01)
(Continued)

(52) U.S. Cl.
CPC ............... *C12M 33/14* (2013.01); *C12M 23/10* (2013.01); *C12M 23/38* (2013.01); *C12M 23/46* (2013.01);
(Continued)

(58) Field of Classification Search
CPC ...... C12M 23/10; C12M 23/38; C12M 33/14; B01D 63/087

USPC ................. 435/297.2, 297.5, 308.1; 210/406, 210/416.1; 422/534
See application file for complete search history.

(56) References Cited

U.S. PATENT DOCUMENTS 2,879,207 A * 3/1959 Poitras ....................... 435/287.7
3,540,856 A * 11/1970 Rochte et al. ................. 422/535
(Continued)

FOREIGN PATENT DOCUMENTS

DE         42 20 560 C1       6/1992
DE    20 2004 001 703 U1      2/2004
(Continued)

*Primary Examiner* — William H Beisner
(74) *Attorney, Agent, or Firm* — Gerald E. Hespos; Michael J. Porco; Matthew T. Hespos

(57) ABSTRACT

The invention relates to a filtration unit, comprising a membrane filter that can be disposed on a filter support of a bottom part and an attachment that can be placed on the bottom part, wherein the membrane filter has a reinforcing edge, and wherein the membrane filter can be clamped to a clamping part of a cover of a culture medium unit for removal purposes and introduced into the culture media unit. The invention further relates to a method for the microbiological analysis of liquid samples following a filtration process, wherein after removing an attachment a membrane filter is lifted off a filter support for pouring in the liquid sample and set down on a surface of a culture medium disposed in the bottom part of a culture medium unit, and the bottom part is covered by a cover. The cover is placed on the membrane resting on the filter support such that a clamping part present on the filter support clamps to a reinforcing edge of the membrane. The cover is lifted off the filter support together with the membrane and placed on the bowl-shaped bottom part such that the bottom of the membrane facing away from the cover rests on the top of the nutrient medium facing the cover.

15 Claims, 3 Drawing Sheets

(51) Int. Cl.
*C12M 1/26* (2006.01)
*C12M 1/00* (2006.01)
*C12M 3/00* (2006.01)
*B01D 63/08* (2006.01)

(52) U.S. Cl.
CPC .......... *B01D 63/087* (2013.01); *B01D 2313/02* (2013.01); *B01D 2313/21* (2013.01); *B01D 2313/56* (2013.01); *B01D 2315/08* (2013.01)
USPC .................... 435/297.5; 435/308.1; 422/534; 210/416.1

(56) References Cited

U.S. PATENT DOCUMENTS

| | | | |
|---|---|---|---|
| 4,668,633 A | 5/1987 | Walton | |
| 5,139,951 A | 8/1992 | Butz et al. | |
| 5,217,619 A * | 6/1993 | Redmond et al. | 210/650 |
| 5,436,151 A | 7/1995 | McGlave et al. | |
| 6,156,566 A | 12/2000 | Bryant | |
| 6,770,203 B2 * | 8/2004 | Leoncavallo et al. | 210/650 |

FOREIGN PATENT DOCUMENTS

| | | |
|---|---|---|
| DE | 10 2005 008 220 B3 | 2/2005 |
| EP | 0 239 697 A2 | 10/1987 |
| EP | 0 463 897 A1 | 1/1992 |
| EP | 0 790 300 A2 | 8/1997 |
| FR | 2 735 496 A1 | 12/1996 |
| FR | 2 820 432 A1 | 8/2002 |
| GB | 2 305 936 A | 4/1997 |
| JP | 09206063 A * | 8/1997 |
| WO | WO 82/00834 | 3/1982 |
| WO | WO 93/24608 | 12/1993 |
| WO | WO 00/19897 | 4/2000 |

* cited by examiner

FILTRATION UNIT AND METHOD FOR THE MICROBIOLOGICAL ANALYSIS OF LIQUID SAMPLES

FIELD OF THE INVENTION

The invention relates to a filtration unit having a membrane filter, which can be arranged on a filter support of a lower part, and an attachment that can be placed on the lower part, and to a nutrient medium unit for holding the membrane filter of the filtration unit having a lower part filled with nutrient medium, and a lid.

Furthermore, the invention relates to a method for the microbiological analysis of liquid samples after prior filtration in the case of which, after the removal of an attachment for the purpose of pouring on the liquid sample, a membrane filter is lifted from the filter support and laid down on a surface of a nutrient medium arranged in a lower part of a nutrient medium unit, and the lower part is covered by a lid.

In order to conduct the microbiological analysis of liquids or samples to be filtered with the aid of a membrane filter, after the filtration the filter is removed and, for example, laid in a Petri dish with a nutrient medium of agar and covered with a lid, wherein the nutrient medium unit is stored in an incubator for a number of days at an elevated temperature. Via the nutrient medium, the possibly present microorganisms obtain nutrients which stimulate growth such that said microorganisms can be determined or counted.

PRIOR ART

Thus, for example, DE 10 2005 008 220 B3 discloses a filtration unit having a membrane filter arranged on a lower part, and having an attachment which can be placed on the lower part.

This device, which has proved itself in principle, has the disadvantage of requiring a special removal ring which can be expanded and used to remove the membrane filter and lay it down in the nutrient medium unit.

Furthermore, DE 198 23 993 B4 discloses a disposable device for determining germ numbers in liquids with the aid of a pouring funnel, a microporous membrane with membrane carrier and a membrane support unit, it being possible to fix the pouring funnel and the membrane carrier to one another, and at least one ejection device for the membrane carrier being provided at the pouring funnel and the membrane carrier and the ejection device being releasably gripped by a membrane support unit.

It is disadvantageous in this case that the filtration unit is of relatively complicated design, and that the filter support must be released after the filtration in a separate step via a defined pressure point. Thereafter, it is necessary in a second additional step for the pouring funnel/membrane carrier unit to be positioned over the open nutrient medium unit, that is to say the agar dish, and for the membrane to be laid down on the nutrient medium by means of a second pressure point offset by 90°.

Furthermore, EP 0 150 775 B1 discloses a device for analyzing a liquid sample by means of membrane filtration, in the case of which the membrane filter is fastened sealingly at the end of a sleeve. This sleeve end is designed such that it serves as a plug-in receptacle for a medium container. The second sleeve end can be tightly closed with a lid in order to put the membrane medium unit into the incubator in a closed state.

A disadvantage here is a fixed connection to the pouring funnel that requires either that a large dead volume be accepted, or else that there be a need for additional handling steps to reduce the dead volume by compression, or else to separate the unit.

OBJECT

An object of the present invention is therefore to provide a device as well as a nutrient medium unit and a method in the case of which it is possible to insert the membrane into the nutrient medium unit simply and cost effectively after the filtration and without the use of an additional aid.

The object relating to the device or filtration unit having a membrane filter is achieved [in conjunction with the preamble of claim 1] by virtue of the fact that the membrane filter has a reinforcing edge, and that the membrane filter can be clamped to a clamping part of a lid of a nutrient medium unit in order to be removed, and can be inserted into the nutrient medium unit.

Because the membrane filter has a reinforcing edge, it can easily be clamped by the lid of a nutrient medium unit that has a clamping part coordinated with the reinforcing edge, can be lifted from the filter support, and can be inserted into the nutrient medium unit. In this case, it is possible on the one hand to use conventional filtration devices, while on the other hand the membrane filter can be inserted into the nutrient medium unit without an additional tool.

In accordance with a preferred embodiment of the invention, the clamping part is designed as an annular inner wall of the lid, the free end, facing the lower part of the nutrient medium unit, of which inner wall can be laid against the reinforcing edge in a clamping fashion. In this case, the free end of the annular inner wall is preferably laid against the reinforcing edge of the membrane filter on the inside.

The annular inner wall of the lid is coordinated its outer diameter with the inside diameter of the reinforcing edge such that upon the placement of the lid on the membrane filter the inner wall slightly expands the reinforcing edge, the result being to produce a clamping connection between the membrane filter and lid. The reinforcing edge can also, for example, have a convex inward bulge that latches into a corresponding concave bulge of the inner wall of the lid. There is no need for an additional tool, since the lid itself serves as a tool.

In order to ensure an adequate exchange of air during incubation for aerobic germs, either the edge region via which the clamping connection is produced is interrupted, or the lid of the nutrient medium unit has an, if appropriate, reclosable additional opening for feeding gas to the membrane surface.

An appropriate airtight, closed version without an opening can be used for anaerobic germs.

In this case, the nutrient medium unit has a dish-shaped lower part that can, for example, be a Petri dish, it being possible to place the lid on the lower part, and arranged in the lower part is a nutrient medium, for example an agar plate, on whose top side facing the lid the membrane filter clamped in the lid can be laid down.

Since the lid with the membrane filter clamped to it is laid down on the top side of the nutrient medium, there is also no need here for an additional tool.

In accordance with a further preferred embodiment of the invention, the top side of the nutrient medium is convexly cambered.

Because the nutrient medium or the agar is convexly cambered, that is to say is higher in the middle, upon placement the membrane firstly makes contact in the middle, and so as the membrane continues to be laid down the air can escape outwards and no air bubbles form. This is desirable since it could otherwise be possible for air bubbles to be included between the membrane and nutrient medium, and this could lead to an inhibition of growth.

However, the formation of air bubbles can also be avoided by virtue of the fact that the membrane filter is cambered towards the nutrient medium by an overpressure in the air space formed between it and the lid.

After the placement of the lid on the lower part the membrane filter and the top side of the nutrient medium lie against one another evenly and without any spacing.

According to a further preferred embodiment of the invention, a support ring which supports the nutrient medium laterally in a lower region and whose inside diameter corresponds approximately to the outside diameter of the membrane filter is arranged concentrically with the outer wall.

The support ring uses less agar, since only the membrane filter surface is underlaid with agar. The reinforcing ring further has the advantage that the surface of the nutrient medium or of the agar plate can more easily be cambered.

In accordance with a further preferred embodiment of the invention, the membrane filter is formed from a flat membrane on which, in order to reinforce its edge on the first side, averted from the filter support, a reinforcing ring forming the reinforcing edge is arranged.

In this case, the reinforcing ring is preferably permanently connected to the membrane by an adhesive or sealing method.

The object with reference to the nutrient medium unit is achieved [in conjunction with the preamble of claim 12] by virtue of the fact that the lid has a clamping part which protrudes into the lower part and can be clamped to a reinforcing edge of the membrane filter in order to remove the membrane filter from the filtration unit.

Because the lid has a clamping part, it is easy for a membrane filter that is coordinated by means of a reinforcing edge with the clamping part of the lid to be clamped, to be lifted from the filter support of a filtration unit, and to be inserted into the lower part of the nutrient medium unit. In this case, on the one hand it is possible to use conventional filtration devices, and on the other hand the membrane filter can be inserted into the nutrient medium unit without an additional tool.

The further task with reference to the method for microbiological analysis of liquid samples after prior filtration is achieved [in conjunction with the preamble of claim 13] by virtue of the fact that the lid is placed on the membrane filter lying on the filter support such that a clamping part arranged in the lid is clamped to a reinforcing edge of the membrane filter, and in that the lid with the membrane filter is lifted from the filter support and placed on the dish-shaped lower part of the nutrient medium unit such that the underside, averted from the lid, of the membrane filter rests on the top side, facing the lid, of the nutrient medium.

Because the membrane filter is clamped to the lid, and the membrane filter is lifted with the lid from the filter support and laid down on the top side of the nutrient medium arranged in the nutrient medium unit, additional steps are avoided and the membrane filter can be moved without an additional tool into the nutrient medium unit.

In accordance with a preferred embodiment of the invention, the lid with the clamped membrane filter is placed on a Petri dish with an agar plate as nutrient medium.

The inventive method can be carried out with the aid of substantially known devices, there only being a need to modify the membrane filter and the lid of the nutrient medium unit in accordance with the invention. The result is a simple and cost effective manipulation of the membrane filter with the applied sample.

Further features of the invention emerge from the following detailed description and the attached drawings in which preferred embodiments of the invention are illustrated by way of example.

DESCRIPTION OF AN EXEMPLARY EMBODIMENT

Figure 1:
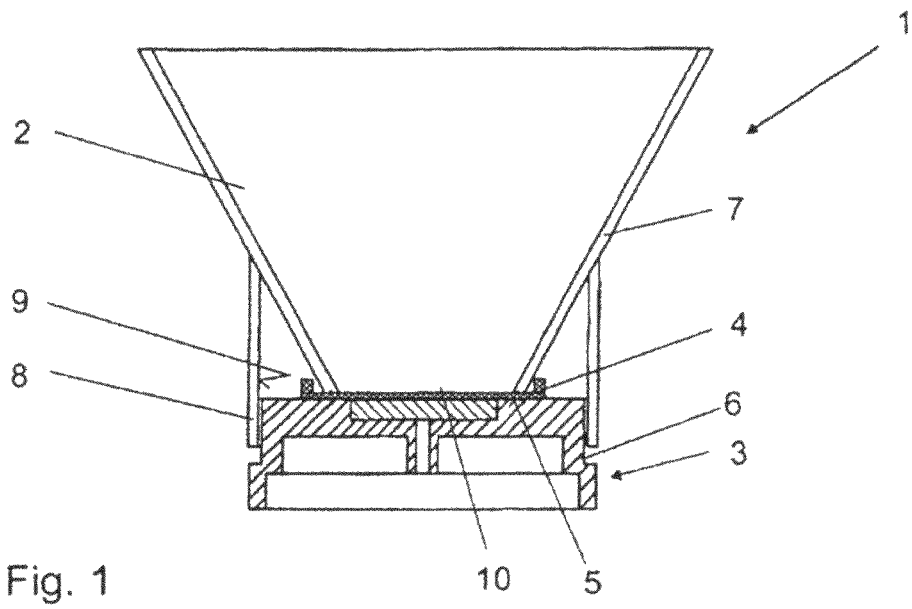
FIG. 1 shows a side view of a filtration unit in section.
Figure 2:
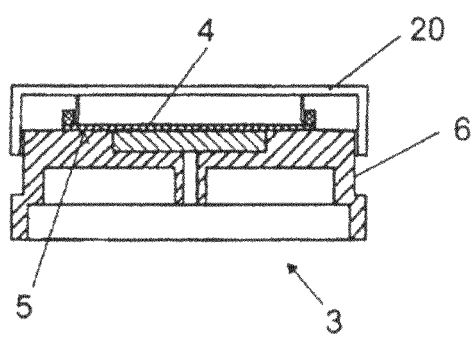
FIG. 2 shows a side view of the lower part from FIG. 1, with membrane filter and the lid of a nutrient medium unit placed on, in section.
Figure 3:
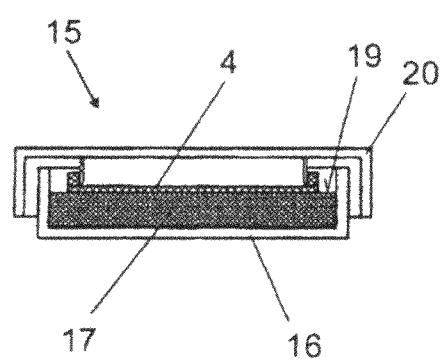
FIG. 3 shows a side view in section of a nutrient medium unit with a lid placed on an a membrane filter inserted.
Figure 4:
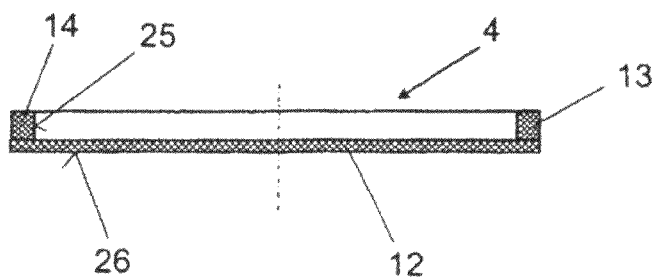
FIG. 4 shows a side view of the membrane filter from FIG. 1, in section and in an enlarged illustration.
Figure 5:
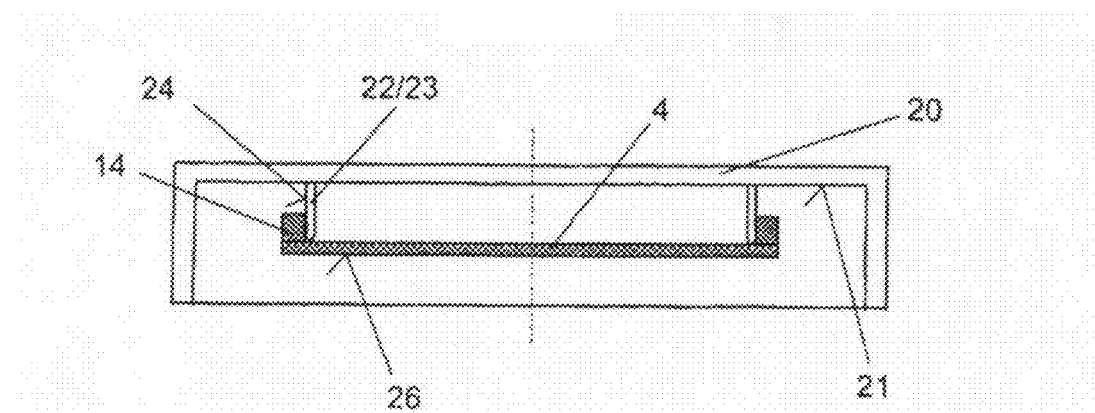
FIG. 5 shows a side view of the lid from FIG. 3 with membrane filter, in section and in an enlarged illustration.

A filtration unit 1 essentially comprises an attachment 2, a lower part 3 and a membrane filter 4.

The lower part 3 has a filter support 5 on which the membrane filter 4 is laid down. The lower part 3 further has a base 6 for holding the attachment 2.

Figure 8:
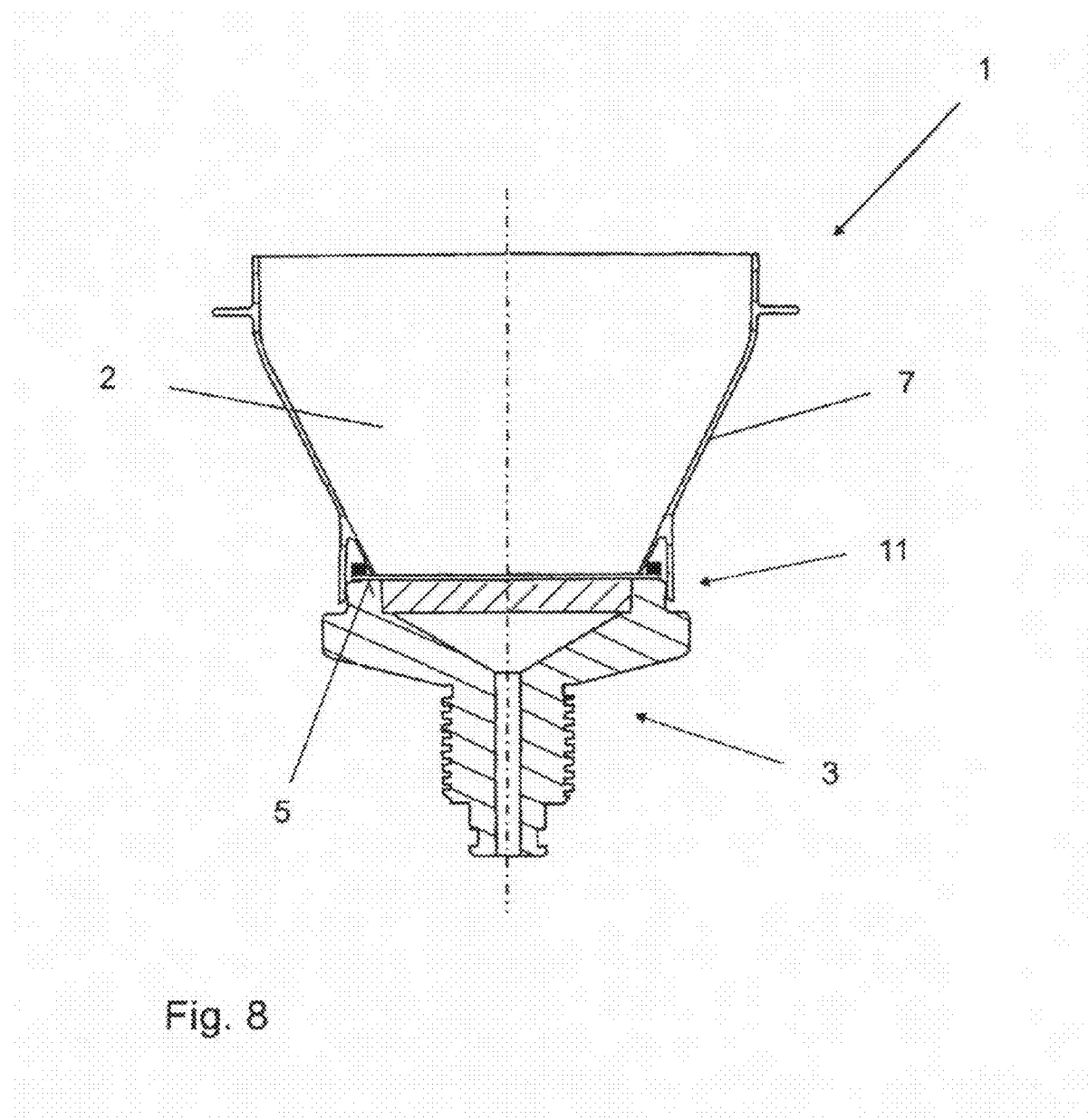
FIG. 8 shows a side view of a further filtration device in section.

The attachment 2 is designed as a funnel 7 that has on its lower end (in a vertical direction) a cylindrical neck 8 that engages with its inner lateral surface 9 over the base of the lower part 3. In the inner region of the cylindrical neck 8, the funnel 7 has an outlet opening 10 that serves as a stop against the lower part 3 or against the membrane filter 4 arranged on the lower part 3. The fixing of the funnel 7 on the lower part 3 is performed by a clamp or, in accordance with FIG. 8, via a latch 11.

The membrane filter 4 comprises a membrane 12 with a reinforcing edge 13. In order to form the reinforcing edge 13, a reinforcing ring 14 is bonded onto the flat membrane 12, or is applied by a sealing method. The membrane filter 4 is clamped with the lower part 3 by the attachment 2 such that the reinforcing edge 13 comes to lie without making contact with the funnel 7 or the inner lateral surface 9 and so the membrane filter 4 remains lying on the lower part 3 after the filtration upon removal of the attachment 2.

After the filtration of the sample, the membrane filter 4 is inserted into a nutrient medium unit 15. The nutrient medium unit 15 has a dish-shaped lower part 16 that can be designed as a Petri dish or an agar plate. A nutrient medium 17, for example made from agar, is arranged in the lower part 16.

Figure 6:
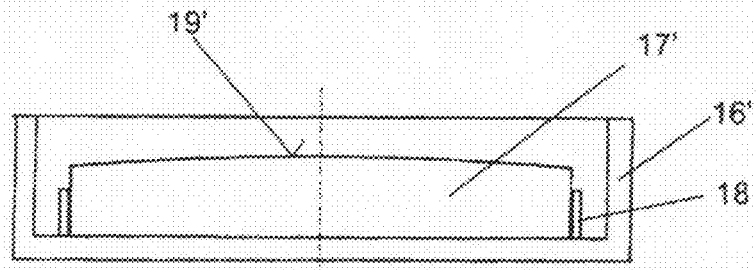
FIG. 6 shows a side view of a nutrient medium unit with a convexly cambered nutrient medium and support ring, in section and in an enlarged illustration.
Figure 7:
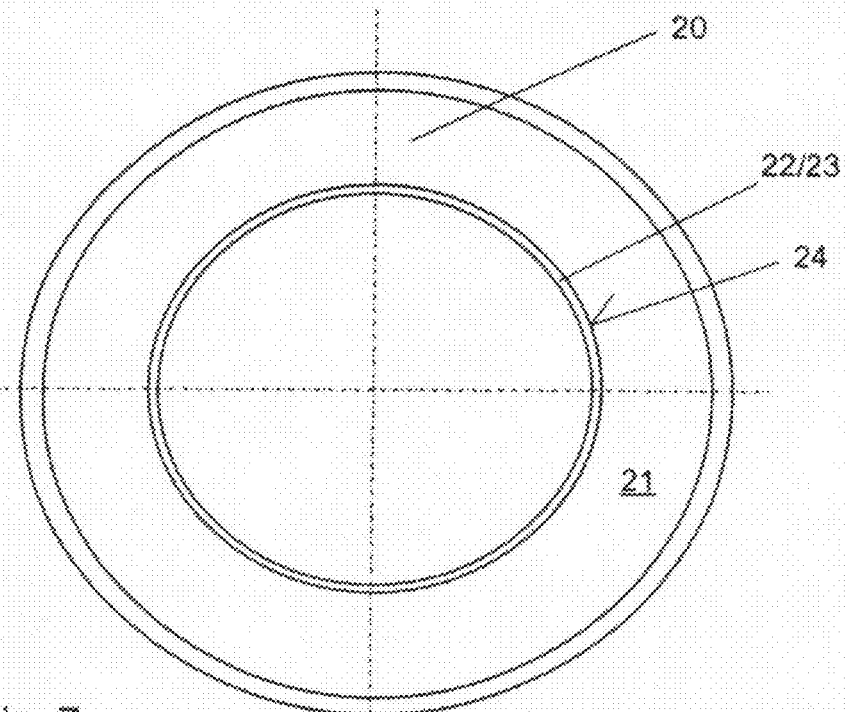
FIG. 7 shows a bottom view of the lid from FIG. 5, in an enlarged illustration.

In accordance with the exemplary embodiment of FIG. 6, the lower part 16' has a support ring 18 that laterally supports the nutrient medium 17' in its lower region. In the unloaded state, the top side 19, 19' of the nutrient medium 17, 17', which is at the top in the vertical direction, is convexly cambered such that the nutrient medium 17, 17' is somewhat thicker towards the middle. The nutrient medium unit 15 has a lid 20 that can be placed on the lower part 16, 16'. On its inner side 21 facing the lower part 16, 16', the lid 20 has a clamping part 22 that is designed as an annular inner wall 23. The free end, facing the lower part 16, of the annular inner wall 23 can be laid on the inside against the reinforcing edge 13 of the membrane filter 4 in a clamping fashion by placing the lid 20 on the membrane filter 4 lying on the filter support 5. Consequently, in the case of the membrane filter 4 held by the lid 20 the annular inner wall 23 or outer surface 24 of the clamping part 22 bears in a clamping fashion against the inner surface 25 of the reinforcing edge 13.

In order to insert the membrane filter 4 into the nutrient medium unit 15, the attachment 2 is lifted from the lower part 3 after the filtering. Subsequently, the lid 20 is removed from the lower part 16, 16' of the nutrient medium unit 15, and placed on the membrane filter 4 lying on the filter support 5 such that the clamping part 22 or the annular inner wall 23 is clamped to the reinforcing edge 13 or the annular inner surface 25 of the membrane filter 4, and the lid 20 is lifted with the membrane filter 4 from the filter support 5 and placed on the lower part 16, 16' of the nutrient medium unit 15. In this case, the lid 20 is placed with the underside 26 of the membrane filter 4 on the top side 19, 19' of the nutrient medium 17, 17'.

The invention claimed is:

1. A filtration assembly for filtration and analysis of liquid samples, the filtration assembly comprising:
   a filtration unit (1) having a lower part (3) with a filter support (5), a membrane filter (4) having an annular reinforcing edge (13), the membrane filter (4) being removably arranged on the filter support (5) of the lower part (3) and an attachment (2) removably placed in the lower part (3) for delivering a liquid sample to the membrane filter (4); and
   a nutrient medium unit (15) having a dish-shaped lower part (16, 16') and a lid (20) selectively engageable with the dish-shaped lower part (16') of the nutrient medium unit (15) when the attachment is removed from the filter support (5), the lid (20) having a clamping part (22) dimensioned for releasable engagement with the annular reinforcing edge (13) of the membrane filter (4) so that the membrane filter (4) can be removed from the filter support (5) of the lower part (3), and can be inserted into the dish-shaped lower part (16, 16') of the nutrient medium unit (15).

2. The filtration assembly of claim 1, wherein the clamping part (22) is an annular inner wall (23) of the lid (20) and has a free end insertable into dish-shaped lower part (16') of the nutrient medium unit (15), the inner wall being dimensioned to be laid against the reinforcing edge (13) of the membrane filter (4) in a clamping fashion.

3. The filtration assembly of claim 2, wherein the free end of the annular inner wall (23) is dimensioned to be laid against an inner circumferential surface of the reinforcing edge (13) of the membrane filter (4).

4. The filtration assembly of claim 1, wherein the dish-shaped lower part (16, 16') contains a nutrient medium (17, 17') having a top side (19, 19') facing the lid (20) when the lid (20) is placed on the dish-shaped lower part (16, 16'), the membrane filter (4) clamped in the lid (20) being laid down in contact with the top side (19, 19') of the nutrient medium (17, 17') when the lid (20) is placed on the dish-shaped lower part (16, 16').

5. The filtration assembly of claim 4, wherein the top side (19, 19') of the nutrient medium (17, 17') is convexly cambered.

6. The filtration assembly of claim 4, wherein the membrane filter (4) is cambered towards the nutrient medium (17, 17') by an overpressure in an air space formed between the membrane filter (4) and the lid (20).

7. The filtration assembly of claim 6, wherein after placement of the lid (20) on the lower part (16) of the nutrient medium unit, the membrane filter (4) and the top side (19, 19') of the nutrient medium (17, 17') lie against one another evenly and without any spacing.

8. The filtration assembly of claim 7, further comprising a support ring (18) which supports the nutrient medium (17') laterally in a lower region and the support ring (18) having an inside diameter corresponding approximately to an outside diameter of the membrane filter (4) and arranged in the lower part (16') concentrically with the outer wall, the support ring (18) surrounding and supporting the nutrient medium (17'), the support ring (18) having an inside diameter corresponding to an outside diameter of the membrane filter (4).

9. The filtration assembly of claim 4, wherein the nutrient medium (17, 17') is formed from agar.

10. The filtration assembly of claim 1, wherein the membrane filter (4) is formed from a flat membrane (12), the reinforcing edge (13) is a reinforcing ring (14) arranged on a side of the flat membrane (12) opposite the filter support (5).

11. The filtration assembly of claim 10, wherein the reinforcing ring (14) is permanently connected to the membrane (12) by an adhesive or sealing method.

12. A filtration assembly for use with a nutrient medium unit (15) having a dish-shaped lower part (16, 16') with a nutrient medium therein, the filtration assembly comprising:
    a lower part (3) with a filter support (5);
    a membrane filter (4) removably arranged on the filter support (5) of the lower part (3), the membrane filter (4) having an annular reinforcing edge (13) with a selected diameter; and
    a lid (20) having a clamping part (22) dimensioned for releasable engagement with the annular reinforcing edge (13) of the membrane filter (4) and dimensioned to be inserted into the dish-shaped lower part (16, 16') of the nutrient medium unit (15) so that the lid (20) can remove the membrane filter (4) from the filter support (5) of the lower part (3) and move the membrane filter (4) into contact with the nutrient medium in the dish-shaped lower part (16') of the nutrient medium unit (15), the lid (20).

13. The filtration unit of claim 12, wherein the clamping part (22) is an annular inner wall (23) of the lid (20) and has a free end insertable into dish-shaped lower part (16') of the nutrient medium unit (15), the inner wall (23) being dimensioned to be laid against the reinforcing edge (13) of the membrane filter (4) in a clamping fashion.

14. The filtration unit of claim 12, wherein the membrane filter (4) is formed from a flat membrane (12), the reinforcing edge (13) is a reinforcing ring (14) arranged on a side of the flat membrane (12) opposite the filter support (5).

15. The filtration unit of claim 14, wherein the reinforcing ring (14) is permanently connected to the membrane (12) by an adhesive or sealing method.

* * * * *